United States Patent
Wunderer et al.

(10) Patent No.: US 9,335,262 B2
(45) Date of Patent: May 10, 2016

(54) GAP DISTRIBUTED BRAGG REFLECTORS

(75) Inventors: Thomas Wunderer, Palo Alto, CA (US); Christopher L. Chua, San Jose, CA (US); Brent S. Krusor, Fremont, CA (US); Noble M. Johnson, Menlo Park, CA (US)

(73) Assignee: PALO ALTO RESEARCH CENTER INCORPORATED, Palo Alto, CA (US)

(*) Notice: Subject to any disclaimer, the term of this patent is extended or adjusted under 35 U.S.C. 154(b) by 1000 days.

(21) Appl. No.: 13/217,859

(22) Filed: Aug. 25, 2011

(65) Prior Publication Data

US 2013/0050686 A1  Feb. 28, 2013

(51) Int. Cl.
| | |
|---|---|
| *G01N 21/41* | (2006.01) |
| *H01S 5/00* | (2006.01) |
| *H01S 3/08* | (2006.01) |
| *H01L 29/06* | (2006.01) |
| *H01L 21/00* | (2006.01) |
| *G02B 5/08* | (2006.01) |
| *B82Y 20/00* | (2011.01) |
| *H01S 5/183* | (2006.01) |
| *H01S 5/343* | (2006.01) |

(52) U.S. Cl.
CPC ........... *G01N 21/41* (2013.01); *B82Y 20/00* (2013.01); *G02B 5/085* (2013.01); *H01S 5/18363* (2013.01); *H01S 5/18308* (2013.01); *H01S 5/18341* (2013.01); *H01S 5/18369* (2013.01); *H01S 5/34333* (2013.01)

(58) Field of Classification Search
CPC ......... H01S 3/00; H01S 3/081; H01S 5/2081; H01S 1/02; H01S 5/18363; H01S 5/18308; H01S 5/18369; H01S 5/34333; H01S 5/18341; H01L 33/10; H01L 33/105; G01N 21/41; G02B 5/085; B82Y 20/00

USPC ........... 372/50.11, 46.014, 99; 257/E33.069; 356/128

See application file for complete search history.

(56) References Cited

U.S. PATENT DOCUMENTS

| | | | | |
|---|---|---|---|---|
| 5,621,750 A * | 4/1997 | Iwano | ................ | H01S 5/18341 372/46.01 |
| 5,703,898 A * | 12/1997 | Ogura | ................ | H01S 5/18305 372/45.01 |
| 5,724,145 A * | 3/1998 | Kondo | ............... | G01B 11/0625 250/559.28 |
| 5,739,945 A | 4/1998 | Tayebati | | |
| 5,848,088 A * | 12/1998 | Mori | ..................... | H01S 5/0262 372/50.21 |
| 6,023,354 A | 2/2000 | Goldstein et al. | | |
| 2004/0048447 A1* | 3/2004 | Kondo | .......................... | 438/458 |
| 2005/0068608 A1* | 3/2005 | Campbell et al. | ............. | 359/291 |
| 2006/0014310 A1* | 1/2006 | Epler | .................... | H01L 33/465 438/22 |
| 2008/0182420 A1* | 7/2008 | Hu et al. | ....................... | 438/712 |
| 2008/0274572 A1* | 11/2008 | Tran | ............................. | 438/29 |

(Continued)

OTHER PUBLICATIONS

Schujman et al., "GaN-ready aluminum nitride substrates for costeffective, very low dislocation density III-nitride LEDs", Jan. 2011, 30 pages.

(Continued)

*Primary Examiner* — Tarifur Chowdhury
*Assistant Examiner* — Sunghee Y Gray
(74) *Attorney, Agent, or Firm* — Hollingsworth Davis, LLC

(57) ABSTRACT

A device includes one or more reflector components. Each reflector component comprises layer pairs of epitaxially grown reflective layers and layers of a non-epitaxial material, such as air. Vias extend through at least some of the layers of the reflector components. The device may include a light emitting layer.

9 Claims, 20 Drawing Sheets

(56) References Cited

U.S. PATENT DOCUMENTS

2010/0316079 A1* 12/2010 Chang-Hasnain et al. 372/45.01
2011/0018104 A1 1/2011 Nagashima et al.

OTHER PUBLICATIONS

Zhou et al., "Accurately nonselective and selective etching of GaAs/$Al_{0.8}Ga_{0.2}As$/AlAs structure for making air-gap cavity", Proc. Of SPIE, vol. 5280, 2004, pp. 889-895.

Sharma et al., "Vertically oriented GaN-based air-gap distributed Bragg reflector structure fabricated using band-gap-selective photoelectrochemical etching", Applied Physics Letters, Vo. 87, 2005, 3 pages.

Khamsehpour et al., "Use of laser reflectometry for end-point detection during the etching of magnetic thin films", J. Vac. Sci. Technol. A 15(4), Jul./Aug. 1997, pp. 2069-2073.

Cho et al., "Control of wet-etching thickness in the vertical cavity surface emitting laser structure by in situ laser reflectometry", J. Vac. Sci. Technol. B 17.6., Nov./Dec. 1999, pp. 2626-2630.

Chu et al., "Emission characteristics of optically pumped GaN-based vertical-cavity surface-emitting lasers", Applied Physics Letters, vol. 89, 121112, 2006, 3 pages.

Cao et al., "Fabrication and performance of blue GaN-based vertical-cavity surface emitting laser employing AlN/GaN and Ta2O5/SiO2 distributed Bragg reflector", Applied Physics Letters, vol. 87, 081105, 2005, 3 pages.

Ng et al., "Distributed Bragg reflectors based on AlN/GaN multilayers", Applied Physics Letters, vol. 74(70, Feb. 15, 1999, 3 pages.

Cho, "GaN Based Heterostructure Growth and Application to Electronic Devices and Gas Sensors", 2009, 251 pages.

Wang et al., "Optically Pumped GaN-based Vertical Cavity Surface Emitting Lasers: Technology and Characteristics", Japanese Journal of Applied Physics vol. 46, No. 8B, 2007, pp. 5397-5407.

Mills, "Expanding horizons for nitride devices & materials", III-Vs Review, vol. 19, No. 1, Feb. 2006 www.three-fives.com, pp. 25-33.

Sharma et al., "Gallium-nitride-based microcavity light-emitting diodes with air-gap distributed Bragg reflectors" Applied Physics Letters, vol. 91, 211108, 2007, 3 pages.

* cited by examiner

GAP DISTRIBUTED BRAGG REFLECTORS

STATEMENT REGARDING FEDERALLY SPONSORED RESEARCH AND DEVELOPMENT

This invention was made with Government support under U.S. Army Cooperative Agreement No. W911NF-10-02-0102 awarded by the Defense Advanced Research Projects Agency (DARPA). The Government has certain rights in this invention.

SUMMARY

Approaches involving gap distributed Bragg reflectors (DBRs) are discussed in this disclosure. Some embodiments illustrate a method of making a semiconductor light emitting device. A light emitting layer, one or more reflective layers, and one or more interstitial layers are epitaxially grown. Each interstitial layer is disposed between two reflective layers. Vias are formed that intersect at least some of the layers. The interstitial layers are exposed to an etchant through the vias and are etched.

Some embodiments are directed to a semiconductor light emitting device. The device includes a light emitting layer and one or more reflector components. Each reflector component comprises alternating epitaxially grown reflective layers and layers of a non-epitaxially grown material. Vias extend through at least some of the layers of the reflector components.

The above summary is not intended to describe each embodiment or every implementation. A more complete understanding will become apparent and appreciated by referring to the following detailed description and claims in conjunction with the accompanying drawings.

DESCRIPTION OF VARIOUS EMBODIMENTS

Figure 1:
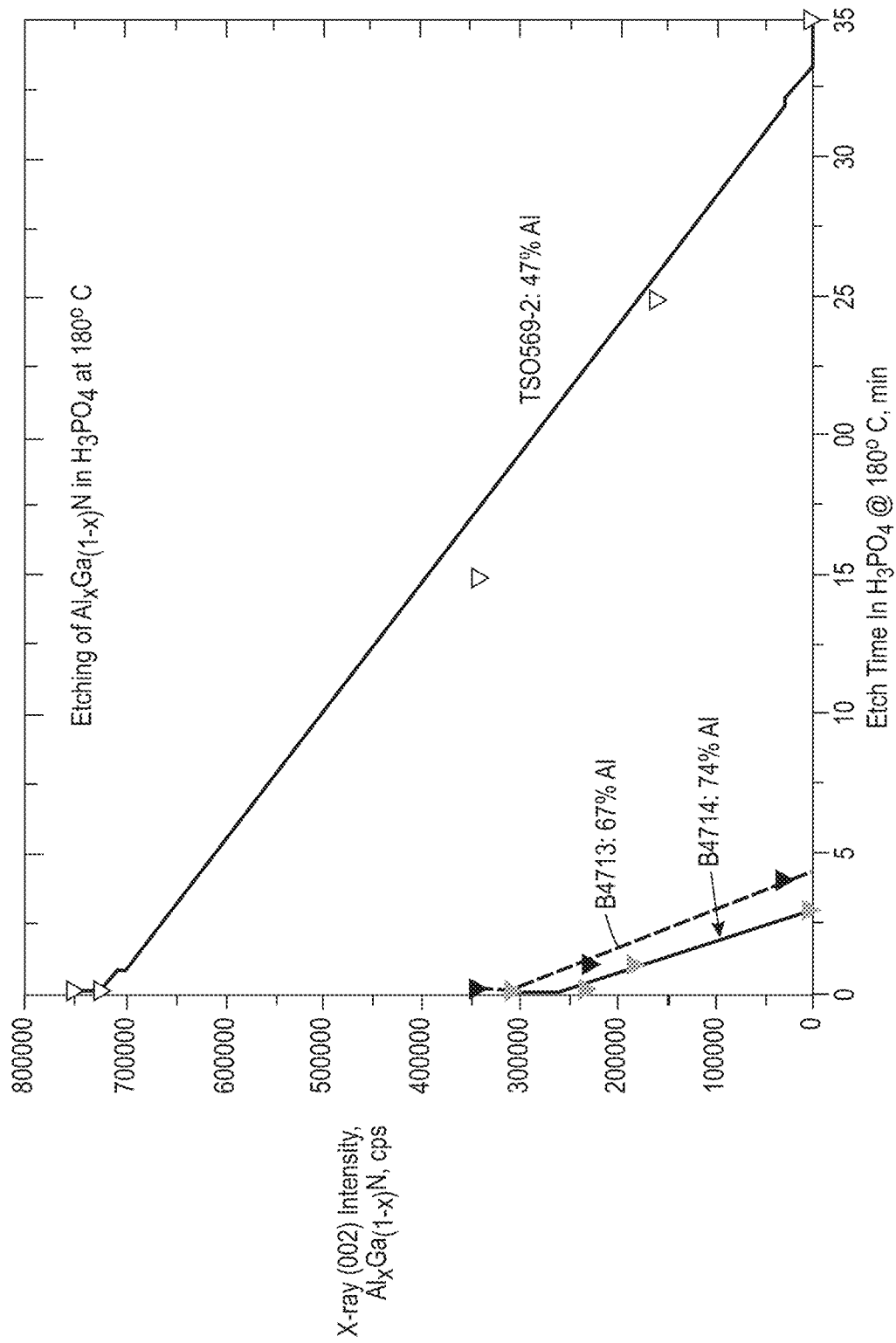
FIG. 1 graphically illustrates etch times of epitaxial $Al_xGa_{(1-x)}N$ layers in phosphoric acid.

Various embodiments involve highly reflective distributed Bragg reflectors (DBRs) and processes for fabricating such DBRs. The DBRs may be useful in vertical cavity surface emitting laser (VCSEL) structures, for example. High reflectivity in the mirror components can provide a lower lasing threshold in semiconductor laser devices. Enhanced reflectivity may be achieved in the DBRs described herein due to the relatively high difference in refractive index provided by the alternating layers. In some embodiments, the DBRs are formed using an alternating stack of reflective and interstitial layers that can be selectively etched.

Embodiments described in this disclosure involve DBRs with interstitial gaps between reflective layers, methods of creating the DBRs, and semiconductor light-emitting devices that include the DBRs. For example, gap DBRs may be formed by growing etchable interstitial alternating with layers that are not etched. At least one sidewall of the interstitial layers is exposed to an etchant. The etchant at least partially removes the interstitial layers between the non-etched reflective layers forming interstitial gaps between the reflective layers. In some embodiments, removal of the interstitial layers involves creating via holes to access the interstitial layers so that they can be exposed to the etchant. Air may occupy the interstitial gaps after the etching.

In DBRs that do not include air gaps, a relatively large number of mirror pairs may be needed because the refractive index difference between the alternating layers is relatively low. Having a large number of mirror pairs may increase the formation of defects and/or may cause the structure to crack due to a high lattice mismatch between the layers of the DBR. The relatively high refractive index difference in a device with nitride-containing layers (e.g., group III-nitrides—(Al—, In—, Ga—, B—)N, or various combinations group III materials and N, such as, AlGaN, InGaN, and InAlGaN, alternating with air gaps can provide a higher overall reflectivity and/or can allow for a reduction in the number of mirror pairs needed to achieve a similar or greater amount of reflectivity than a device without air gaps.

The devices formed according to the approaches described herein can have a reflectivity greater than 99% with fewer than 20 reflector pairs or even fewer than 5 reflector pairs. For example, the reflectivity, R, at the interface between an AlN and a GaN layer at a wavelength of 350 nm is less than about 1%, whereas at a GaN/air interface, R is as high as about 21.3% (the index of refraction for GaN is n_GaN=2.713, the index of refraction for AlN is n_AlN=2.225, and the index of refraction for air is about 1). The difference in refractive index may be greater than 0.6 for layer pairs that include an epitaxially grown reflective layer and a non-epitaxial material disposed in the interstitial gaps between the reflective layers. In some cases, the second material may be air. In some cases, there may be a vacuum in the interstitial gaps.

In some implementations, a material other than air may be present in the gaps between the reflective layers. For example, the DBR may be configured to function as a sensor wherein the optical characteristics of the DBR properties change based on a presence and/or one or more characteristics (e.g., temperature, pressure, or concentration) of an analyte. DBR sensors and systems are described more fully below.

In examples described below, alternating layers of GaN and etchable AlGaN are described as the reflective and etchable interstitial layers, respectively. It will be appreciated that other materials may be used to create the DBRs discussed herein so long as the material of the interstitial layer can be selectively etched while the material of the reflective layer remains intact. Generally, the interstitial layers may be referred to as etchable layers and the reflective layers may be referred to as non-etchable layers. This terminology is intended to convey that the etchable layers are relatively more easily etchable than the non-etchable layers using the etchants and/or etching processes described herein.

Figure 2:
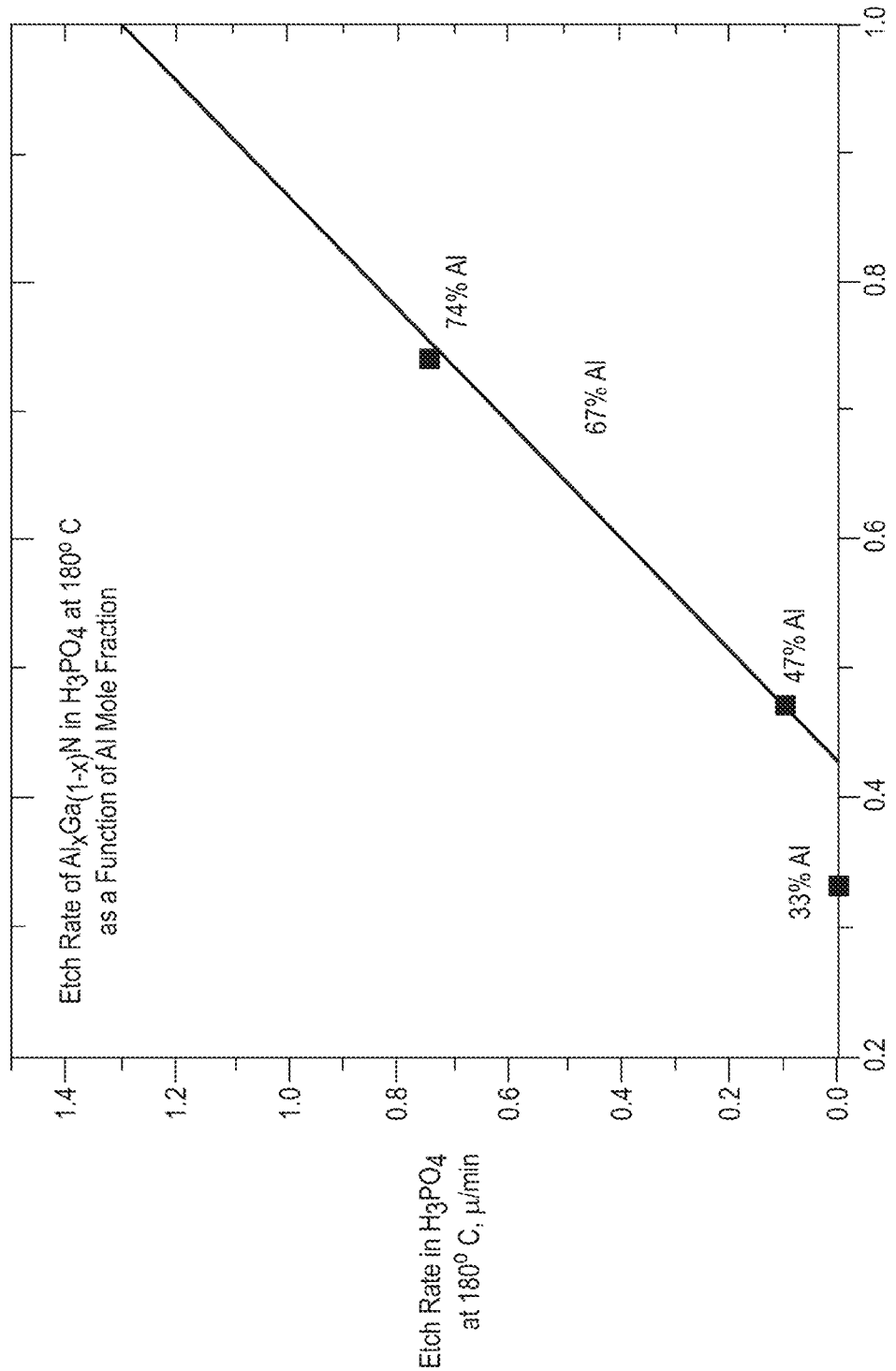
FIG. 2 is a graph of the etch rate of $Al_xGa_{(1-x)}N$ layers in phosphoric acid.

Selectively etching AlN or AlGaN in the DBR structures is possible because of the differential etch rates of GaN (or AlGaN having low aluminum content) as compared to AlN (or AlGaN layers having higher aluminum content). The etch rate of AlGaN materials varies as a function of aluminum content. FIGS. 1 and 2 are graphs illustrating etch times and etch rate, respectively, of epitaxially grown AlGaN layers as a function of mole fraction of aluminum. For each sample, the thickness of the AlGaN layer being etched was monitored by periodically taking the sample out of the chemical bath etchant and performing x-ray scans to determine the x-ray signal intensity of the AlGaN layer. FIG. 1 shows etch times of epitaxial $Al_xGa_{(1-x)}N$ layers having a thickness of about 1.9 µm etched in phosphoric acid ($H_3PO_4$) at a concentration 92% and temperature of 180° C. The layers of AlGaN having aluminum mole fraction of 74% or 67% were substantially removed in less than 5 min., whereas the AlGaN layer having 47% aluminum mole fraction took over 30 min. to remove.

FIG. 2 shows a graph of the etch rate of $Al_xGa_{(1-x)}N$ in $H_3PO_4$ at a concentration of 92% and temperature of 180° C. as a function of aluminum mole fraction. The graph shows that the etch rate increases with increasing aluminum mole fraction.

Figure 3:
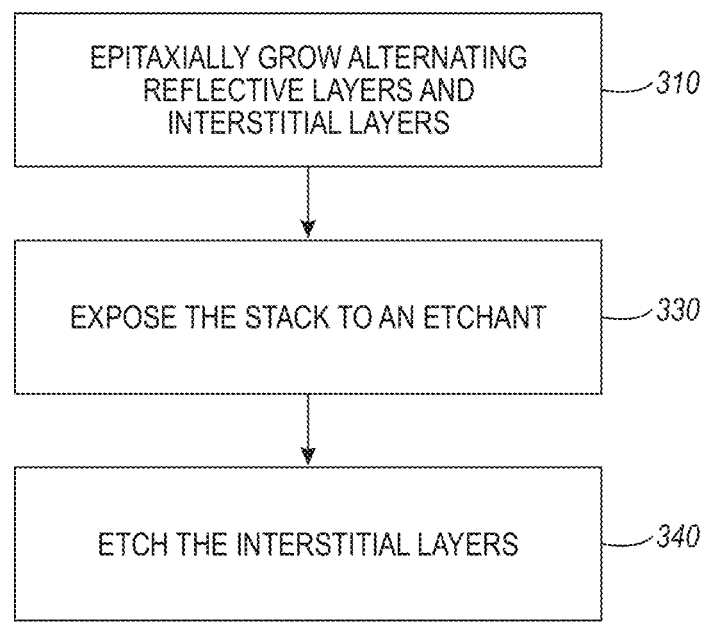
FIG. 3 is a flow diagram illustrating a method of forming a device comprising a gap distributed Bragg reflector (DBR) in accordance with embodiments described herein.

FIG. 3 is a flow diagram illustrating a method of forming a device comprising a gap DBR in accordance with embodiments described herein. A stack of alternating etchable interstitial layers and non-etchable reflective layers is epitaxially grown 310. The stack is exposed 330 to an etchant which etches the interstitial layers. The interstitial layers are etched 340 for a predetermined period of time. During this time period, the interstitial layers may be partially or fully removed. Removal of the interstitial layers creates interstitial gaps between the reflective layers, which may be occupied by a second material, such as air. The reflective and/or interstitial layers may comprise group III-nitride materials such as (Al—, Ga—, In—, B—)N or any combination of group III elements and nitrogen, e.g., AlGaN, InGaN, InAlGaN, etc. In some cases, the one or more reflective layers comprise gallium nitride (GaN) and the one or more interstitial layers comprise aluminum gallium nitride (AlGaN) having an aluminum content sufficient to allow etching. The GaN/air gap pairs formed by the etching can provide a higher refractive index difference as compared to the refractive index difference achieved with GaN/AlGaN pairs. As previously mentioned, the higher refractive index contrast between the reflective layers and the air gaps allows a device to be grown with fewer reflective layers for a similar and/or greater amount of reflectivity.

Figure 4:
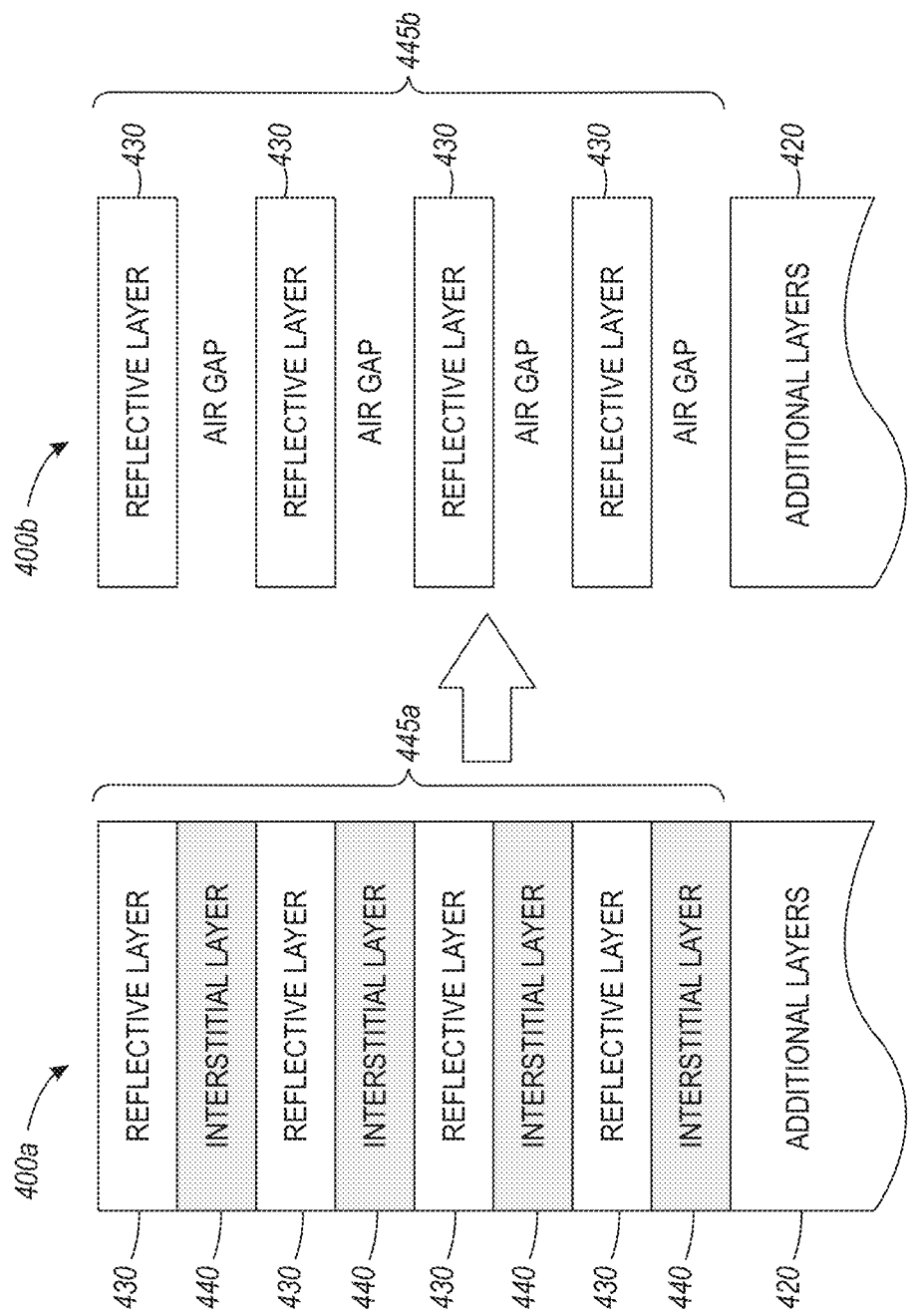
FIG. 4 is a diagram that illustrates a process for forming a gap DBR before and after the removal of the interstitial layers in accordance with embodiments described herein.

FIG. 4 is a diagram that illustrates a gap DBR before and after the removal of the interstitial layers. Before removal of the interstitial layers, the device 400a includes one or more interstitial layer/reflective layer pairs 440/430. The device 400 may include one or more additional layers 420. The additional layers 420 can provide a base for the epitaxial growth of the interstitial layer/reflective layer pairs 440/430 and/or the additional layers 420 can be grown on the interstitial layer/reflective layer pairs 440/430. Four interstitial layer/reflective layer 440/430 pairs are shown in the device 400a of FIG. 4. The interstitial layers 440 may be selectively etched away by a wet etchant such as hot phosphoric acid, as described previously. After removal of the interstitial layers 440 by the etching process, interstitial gaps form between the reflective layers 430. The interstitial gaps (which may be occupied by a material such as air) are sandwiched between reflective layers 430 make up a reflective region 445 of the device 400b. The reflectivity of region 445b of device 400b is greater than the reflectivity of region 445a of device 400a. The thickness of the reflective and air layers is related to the target wavelength of interest. In general, the target wavelength can be any wavelength, however, a target wavelength range of 350 to 600 nm is of interest for many implementations. For example, the layer thickness d=(m*λ)/(4*n), where m is equal to 1, 3, 5, 7, λ is the target wavelength, and n is the refractive index. For blue light (λ=460 nm) and GaN/AlGaN reflective/interstitial layers, the thickness of a GaN reflective layer d_GaN=460/(4*2.476)=46.4 nm and the thickness of the AlGaN interstitial layer d_AlGaN=d_air=460/4=115 nm.

Figure 5:
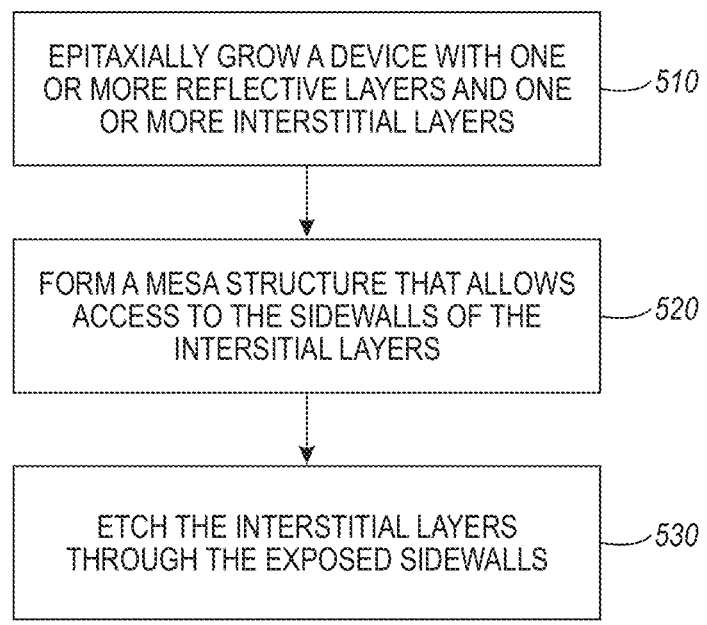
FIG. 5 is a flow diagram that shows a process for forming a mesa structure that allows access to the sidewalls of the interstitial layers by an etchant in accordance with various embodiments.
Figure 6:
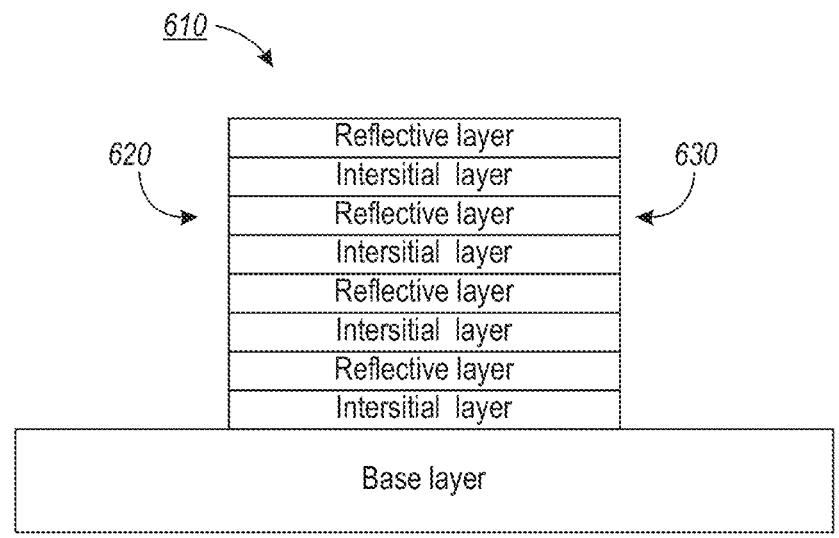
FIG. 6 is an example of a mesa structure that exposes at least one sidewall of the interstitial layers in accordance with embodiments described herein.
Figure 7:
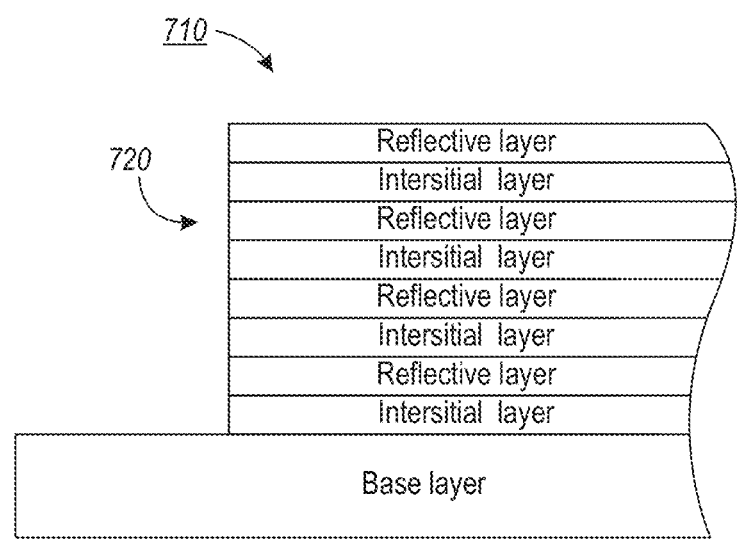
FIG. 7 is another example of a mesa structure that exposes at least one sidewall of the interstitial layers in accordance with embodiments described herein.

The ability to etch the interstitial layers may rely on accessing at least one sidewall of interstitial layer so that each interstitial layer can be exposed to the etchant. One way to access sidewalls of the interstitial layers is to epitaxially grow interstitial layer/reflective layer pairs 510 followed by formation of a mesa structure 520, as illustrated by the flow diagram of FIG. 5. Formation of the mesa structure may involve etching a mesa structure, e.g., mesa stripe, into the epitaxially grown layers. Etching the mesa stripe is accomplished by non-selective etching of both the reflective and interstitial layers. The mesa structure allows access to sidewalls of the interstitial layers. The sidewalls of the interstitial layers (made accessible by the mesa structure) are exposed 530 to a wet etchant during an etching process that selectively etches the interstitial layer and leaves the reflective layers intact. Formation of a mesa structure 610 may allow access to two sidewalls 620, 630 of the interstitial layers as shown in FIG. 6. Alternatively, only one sidewall 720 of the interstitial layers may be accessed by formation of a step structure 710 as illustrated in FIG. 7.

Figure 8:
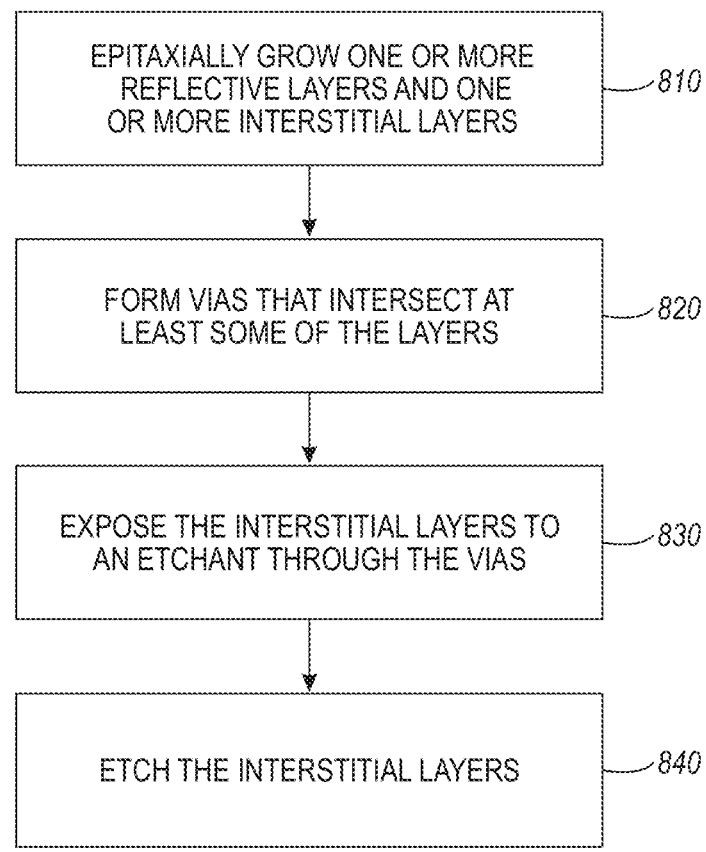
FIG. 8 is a flow diagram that illustrates a process for forming a vias that expose the interstitial layers to an etchant in accordance with various embodiments.

In some processes, access to the interstitial layers may be achieved through one or more via holes as illustrated in the flow diagram of FIG. 8. Pairs of reflective layers and interstitial layers are epitaxially grown 810. One or more vias are formed 820 that penetrate the reflective layers and the interstitial layers. The one or more vias can be created using a non-selective dry etching process. For example, the vias may be created by using electron cyclotron resonance (ECR), inductively coupled plasma (ICP), reactive ion etching (RIE), chemically-assisted reactive ion etching (CAIBE), and/or processes. The creation of the one or more vias allows access to the interstitial layers which are exposed 830 to a wet etchant, e.g. phosphoric acid. The interstitial layers are partially or fully etched 840 by the etchant. In some cases, interstitial layers may be etched for a period of time that is selected to achieve a predetermined amount of etching. The characteristics of the layer stack may be used to control the etching process. For example, in some implementations, the color and/or reflectivity of the layer stack is monitored during the wet etching process and etching is controlled, e.g., the etching rate may be decreased or stopped once a certain color and/or reflectivity is reached.

Figure 9:
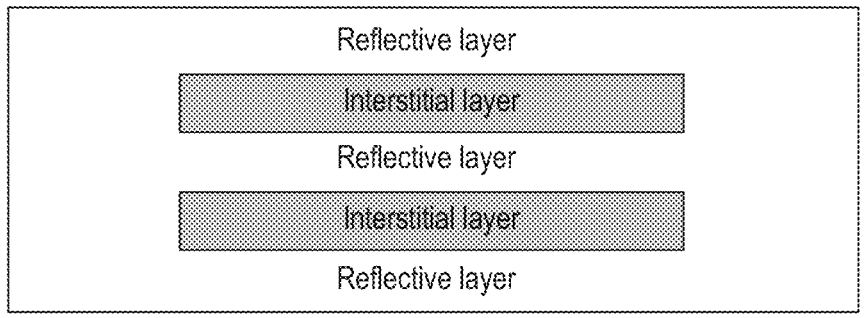
FIG. 9 illustrates a device with one or more reflective layers and one or more interstitial layers in accordance with embodiments described herein.
Figure 10:
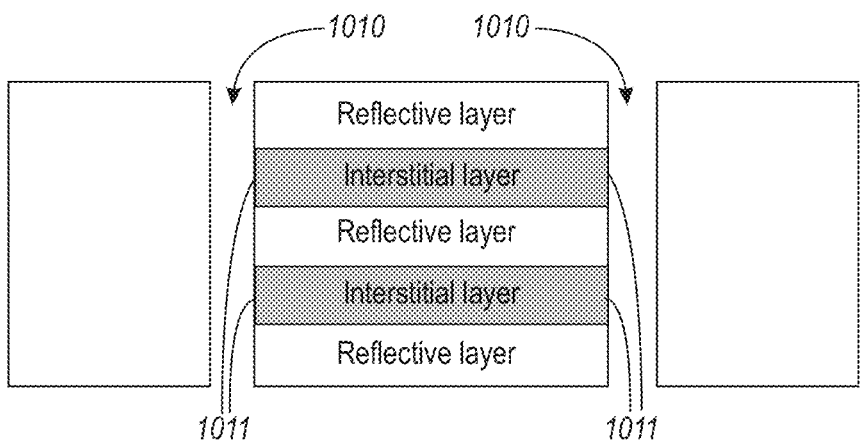
FIG. 10 shows a device with one or more reflective layers, one or more interstitial layers, and vias that expose the interstitial layers to an etchant in accordance with embodiments described herein.
Figure 11:
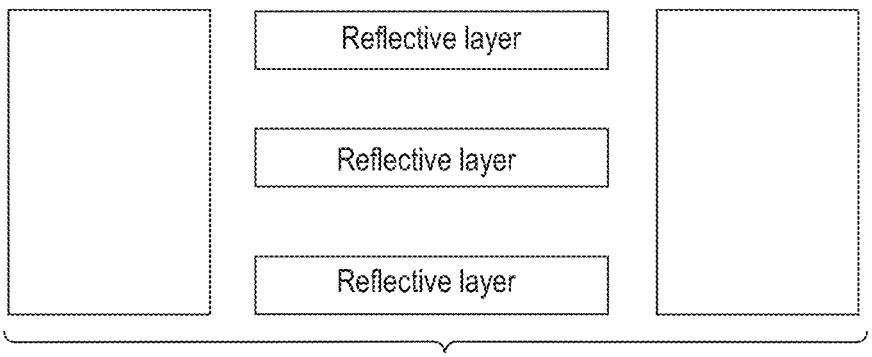
FIG. 11 is a device with one or more reflective layers and air gaps sandwiched between the reflective layers in accordance with embodiments described herein.

FIGS. 9-11 illustrate a process for creating vias to expose one or more interstitial layers to an etchant in accordance with embodiments described herein. FIG. 9 illustrates a layer stack having alternating reflective layers and interstitial layers. FIG. 10 shows the creation of vias 1010 in the layer stack of FIG. 9. The vias can be etched using a non-selective etching process, as described previously, e.g., a wet or dry etching process, which etches both the reflective and non-reflective layers. As can be observed from FIG. 10, the vias allow access to the sidewalls 1011 of the layer stack. FIG. 10 shows the two vias 1010, but it will be appreciated that more or fewer vias may be created. In some cases, the vias may only penetrate through some of the reflective/interstitial layer pairs in the layer stack. Exposing a sidewall 1011 of the interstitial layers may alternatively or additionally include creating vias in conjunction with the creation of a mesa structure such that a first subset of the interstitial layers have a sidewalls that are accessed by the creation of the mesa structure and a second subset of the interstitial layers are accessed through the creation of vias. FIG. 11 illustrates a cross-section of a layer stack after the one or more interstitial layers have been etched by exposure of the interstitial layers to an etchant that flows into the vias. The interstitial layers are replaced by interstitial gaps, e.g., air gaps that have a higher refractive index difference with the reflective layers, thus increasing the reflectivity of the layer stack.

Figure 12:
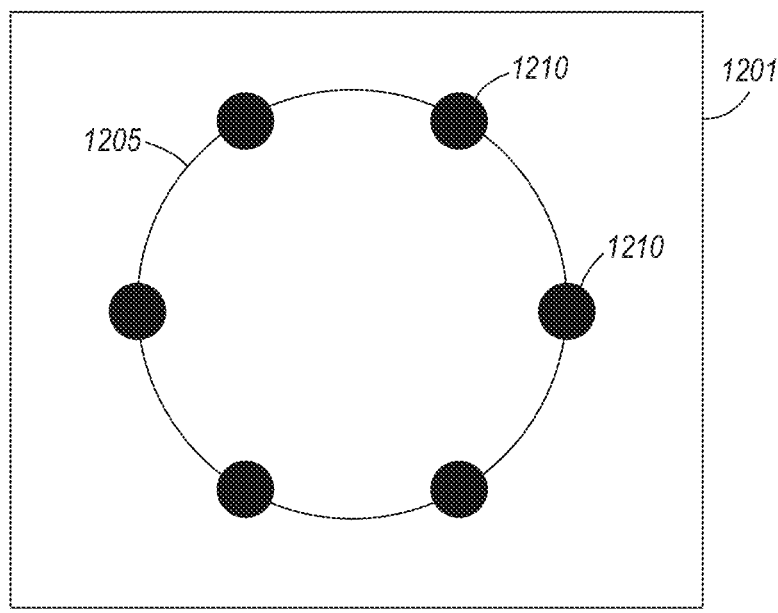
FIG. 12 illustrates a device with vias that are oriented to surround a central region in accordance with embodiments described herein.
Figure 13:
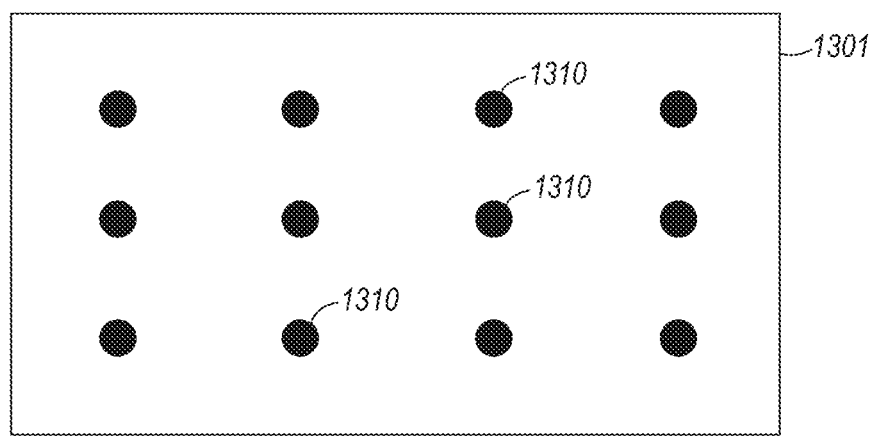
FIG. 13 shows an example in which the vias have a linear orientation and are oriented in one or more rows on the device in accordance with various embodiments.

The one or more vias may be formed in any arrangement and may be created through any surface of the device. FIG. 12 shows a top view 1201 of a device. In this example, the vias 1210 are oriented to surround a central region 1205 of the device. The vias may be created on the top and/or the bottom surfaces of the device, for example. The orientation shown in FIG. 12 provides a high reflectivity area in the central region 1205 after the interstitial layers are etched. In some cases, the one or more vias may be oriented in a linear pattern along one or more sides of the device. FIG. 13 illustrates an example in which the vias have a linear orientation and are oriented in one or more rows along a surface 1301 of the device. Note that the device may have more or fewer vias than as depicted in FIGS. 12 and 13

Figure 14:
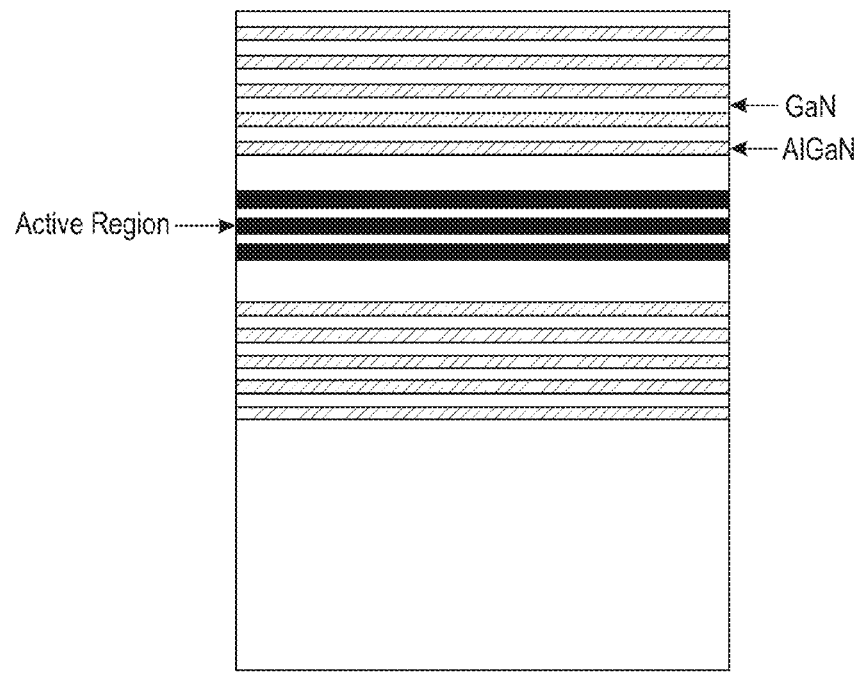
FIG. 14 illustrates a device with a light emitting layer, one or more reflective layers, and one or more interstitial layers in accordance with various embodiments.
Figure 15:
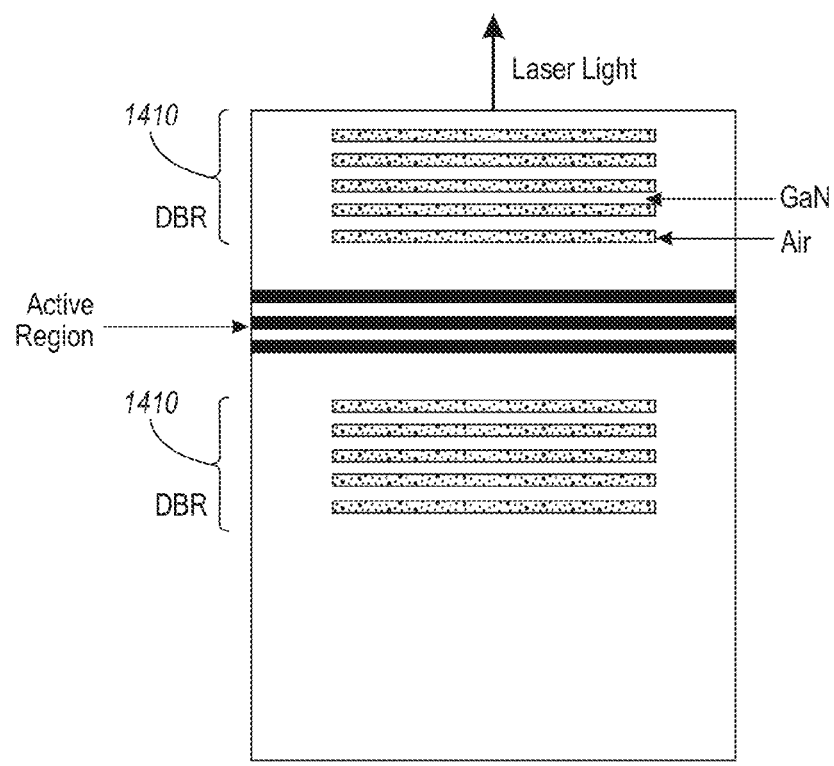
FIG. 15 is a device with a light emitting layer, one or more reflective layers, and one or more air gaps oriented between the reflective layers in accordance with various embodiments.

Various devices described herein include a light emitting-layer an addition to one or more reflective regions. FIGS. 14 and 15 illustrate a device having a light emitting layer between two reflective regions in accordance with embodiments described herein. In FIGS. 14 and 15, the reflective layers comprise GaN and the interstitial layers comprise AlGaN. Additionally or alternatively, the reflective and/or the interstitial layers may comprise other materials. FIG. 14 illustrates two regions before etching having alternating GaN reflective layers and AlGaN interstitial layers. The light emitting layer comprises three quantum wells. One of the reflective regions is below the light emitting layer and one is above the light emitting layer.

The interstitial layers can be exposed to a wet etchant by exposing sidewalls by the formation of a mesa structure and/or the formation of vias that intersect the interstitial layers, for example. FIG. 15 illustrates the device of FIG. 14 after the interstitial layers are etched. The interstitial layers may be exposed to the etchant for a period of time based on etch rate. As can be observed in FIG. 15, interstitial gaps are left in the place of the AlGaN. The interstitial gaps can be occupied by air to form air gap DBRs 1410 with the reflective GaN layers.

Figure 16:
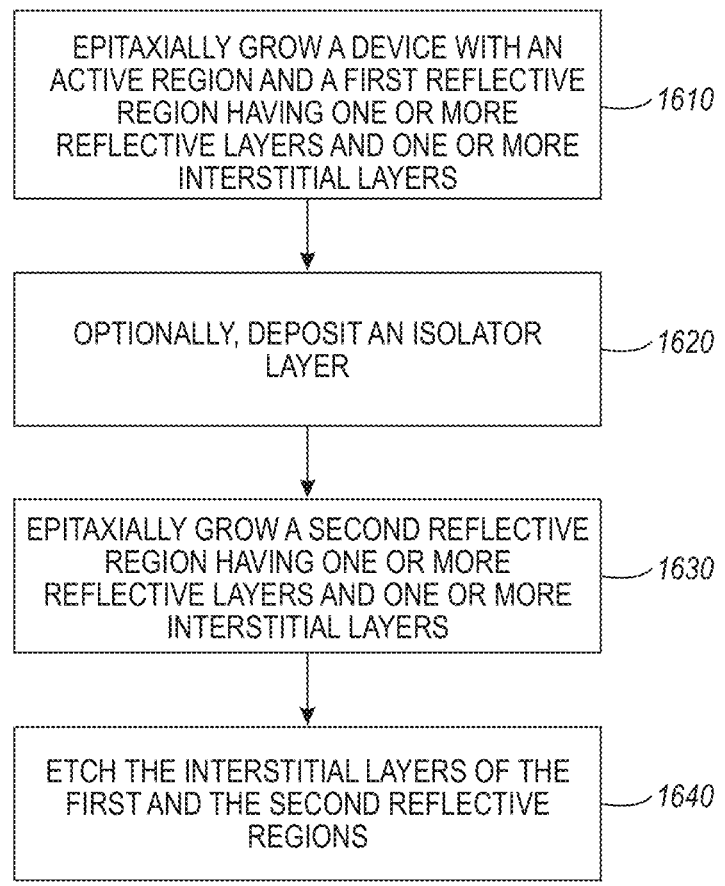
FIG. 16 shows a flow diagram of a method of making a device with a light emitting layer in accordance with various implementations.

FIG. 16 is a flow diagram of a method of making a device with a light emitting layer in accordance with various embodiments. A device with a light emitting layer and a first reflective region is grown 1610 in a first epitaxial growth session. The first reflective region comprises one or more reflective layers and one or more interstitial layers. Optionally, an isolator layer is deposited 1620 that provides current confinement within the device. The isolator layer may comprise $SiO_2$, for example, and is deposited using evaporation and/or sputtering techniques. In some cases, a thin interstitial layer is grown and/or deposited in place of the isolator. The interstitial layer can be partially etched and/or oxidized to enhance current confinement. A second reflective region having one or more reflective regions and one or more interstitial regions is grown 1630 in a second epitaxial growth session. The interstitial layers of the first and the second reflective regions are etched 1640.

Figure 17:
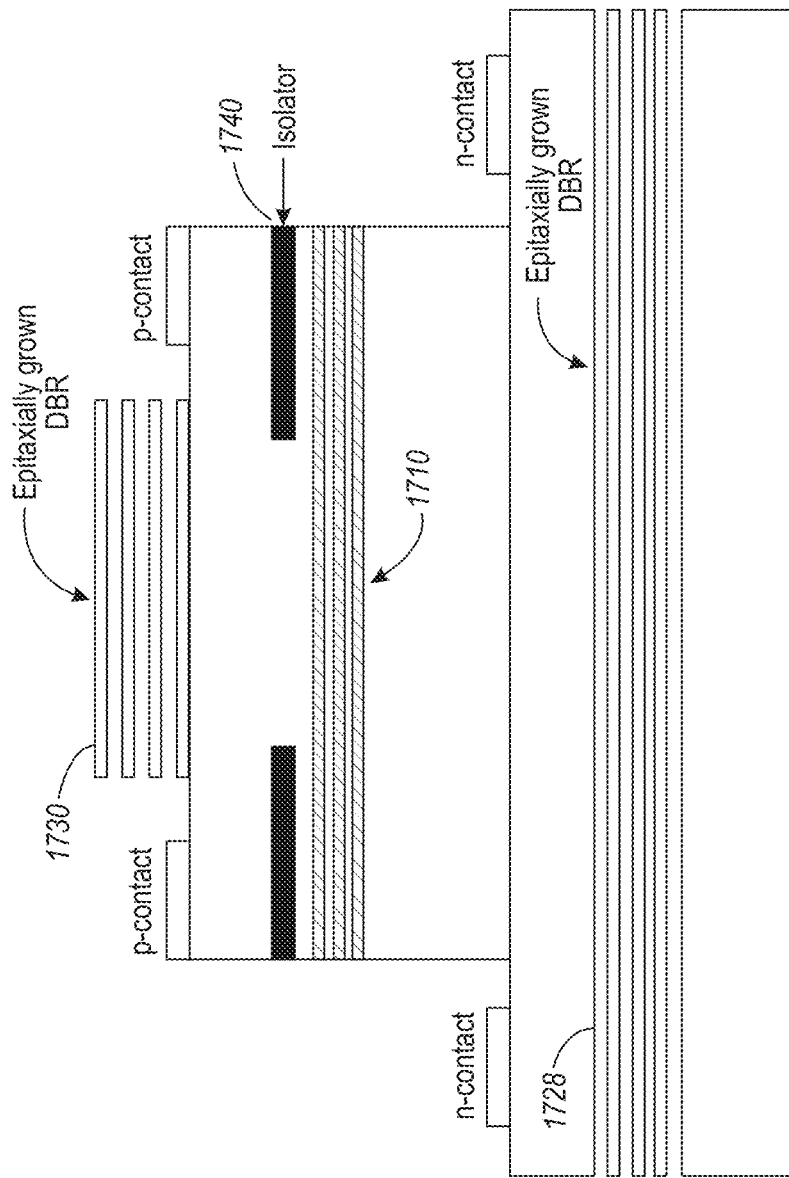
FIG. 17 is a schematic diagram of a device having a light emitting layer and two epitaxially-grown reflective regions in accordance with embodiments described herein.

The process of FIG. 16 can be used to create a device depicted in FIG. 17, for example. The heterostructure illustrated in FIG. 17 may be grown by metal organic vapor epitaxy to include a multiple quantum well (MQW) light-emitting layer 1710, two epitaxially-grown reflective regions 1720, 1730 and an isolator 1740. As described in the discussion of FIG. 16, the first reflective region 1720 and the light emitting layer 1710 are grown in a first epitaxial grown session. The isolator 1740 is deposited and a second epitaxial growth session creates the second reflective region 1730. FIG. 17 shows the reflective regions 1720, 1730 with the interstitial layers etched. In some cases, one etching process etches the interstitial layers for the first reflective region 1720 and a second etching process etches the layers for the second reflective region 1720. For example, the first etching process may etch the interstitial layers for the first reflective region 1720 before the growth of the light emitting layer and the second etching process etches the interstitial layers in the second reflective region 1730.

Figure 18:
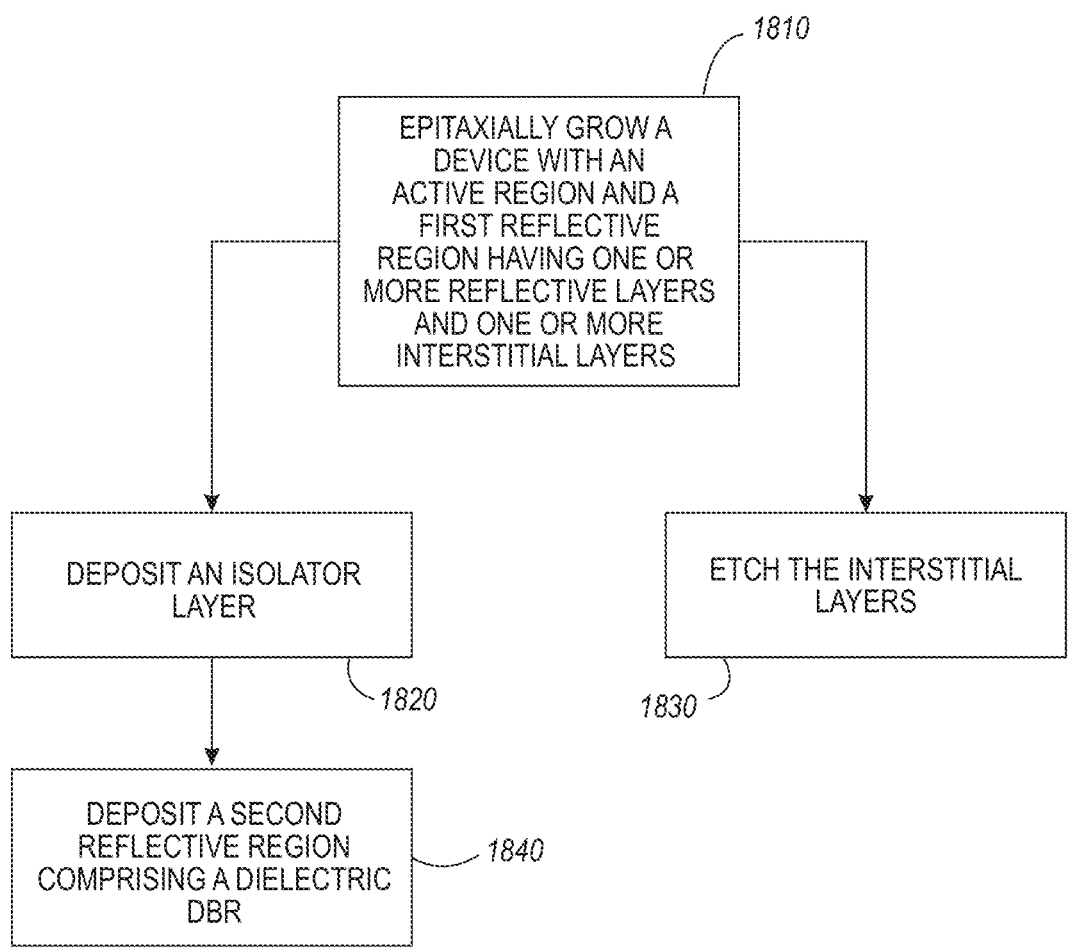
FIG. 18 is a flow diagram of a method of making a device with a light emitting layer in accordance with embodiments described herein.

FIG. 18 is a flow diagram of a method of making a device with a light emitting layer in accordance with various implementations. A device with a light emitting layer and a first reflective region is grown 1810. The first reflective region comprises one or more reflective layers and one or more interstitial layers. An isolator layer and a second reflective region are deposited 1820, 1840. A contact layer, e.g., comprising ITO, for example, may also be deposited. The isolator layer may comprise $SiO_2$ and the second reflective region may comprise alternating layers of $SiO_2$ and $TiO_2$, for example. The interstitial layers of the first reflective region are etched 1830. The second reflective region is deposited using evaporation or sputtering, for example. The interstitial layers of the first reflective region may be etched before or after the deposition of the second reflective region.

Figure 19:
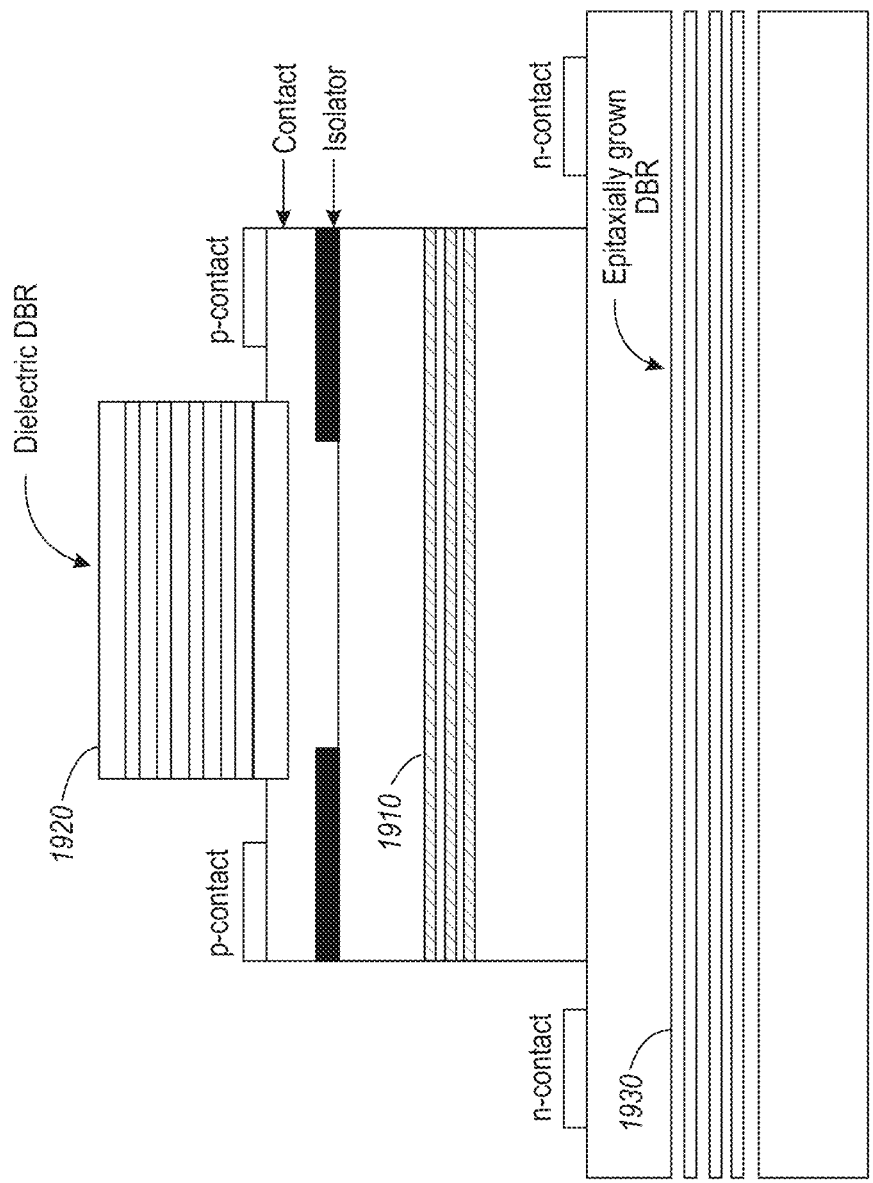
FIG. 19 is a schematic diagram of a device having an active region, an epitaxially grown reflective region, and a dielectric reflective region in accordance with various embodiments.

FIG. 19 illustrates a device that may be fabricated using the method of FIG. 18. The device of FIG. 19 comprises a light-emitting layer 1810, a first reflective region 1830 that is epitaxially grown, and a second reflective region 1820 that is deposited. As described above, the second reflective region 1820 may be a dielectric DBR comprising alternating deposited layers of $SiO_2$ and $TiO_2$, and/or other materials. The interstitial layers in the first reflective region 1830 may be etched before or after the growth of the light emitting layer and/or the deposition of the second reflective layer.

Figure 20:
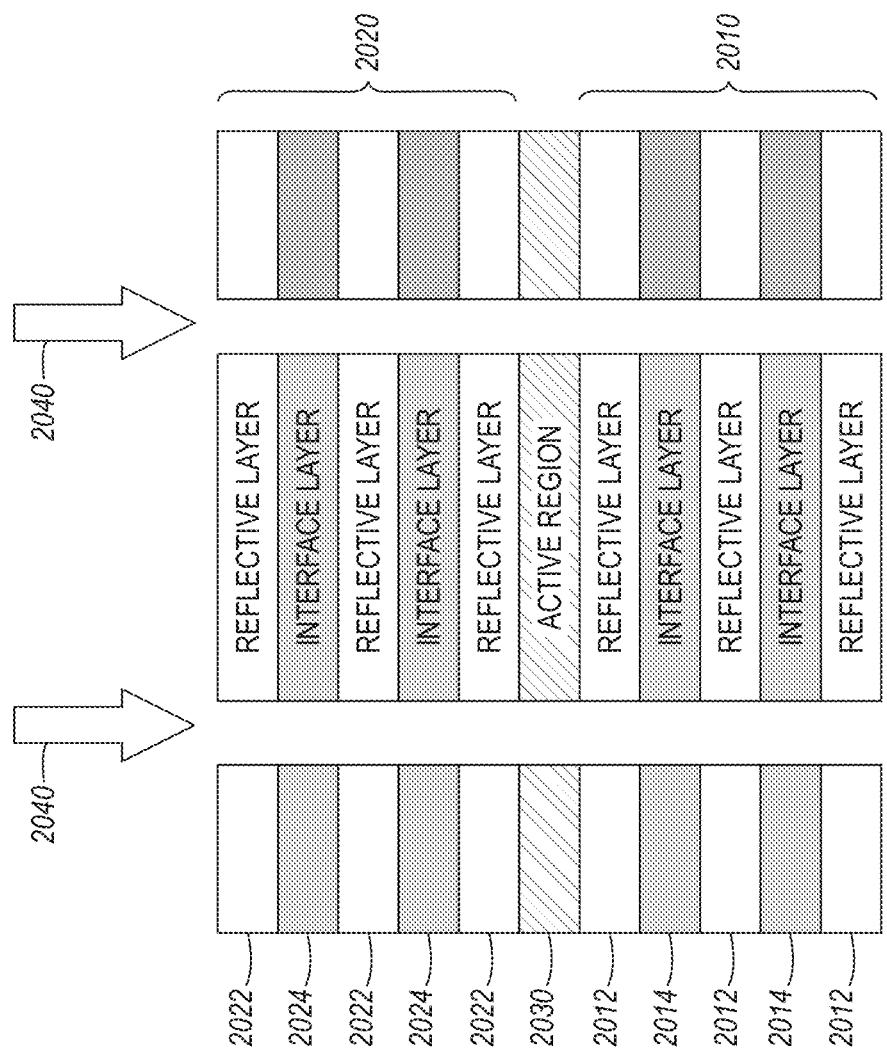
FIG. 20 illustrates a device in which one set of vias allows access by an etchant to the interstitial layers of two reflective regions in accordance with embodiments described herein.
Figure 21:
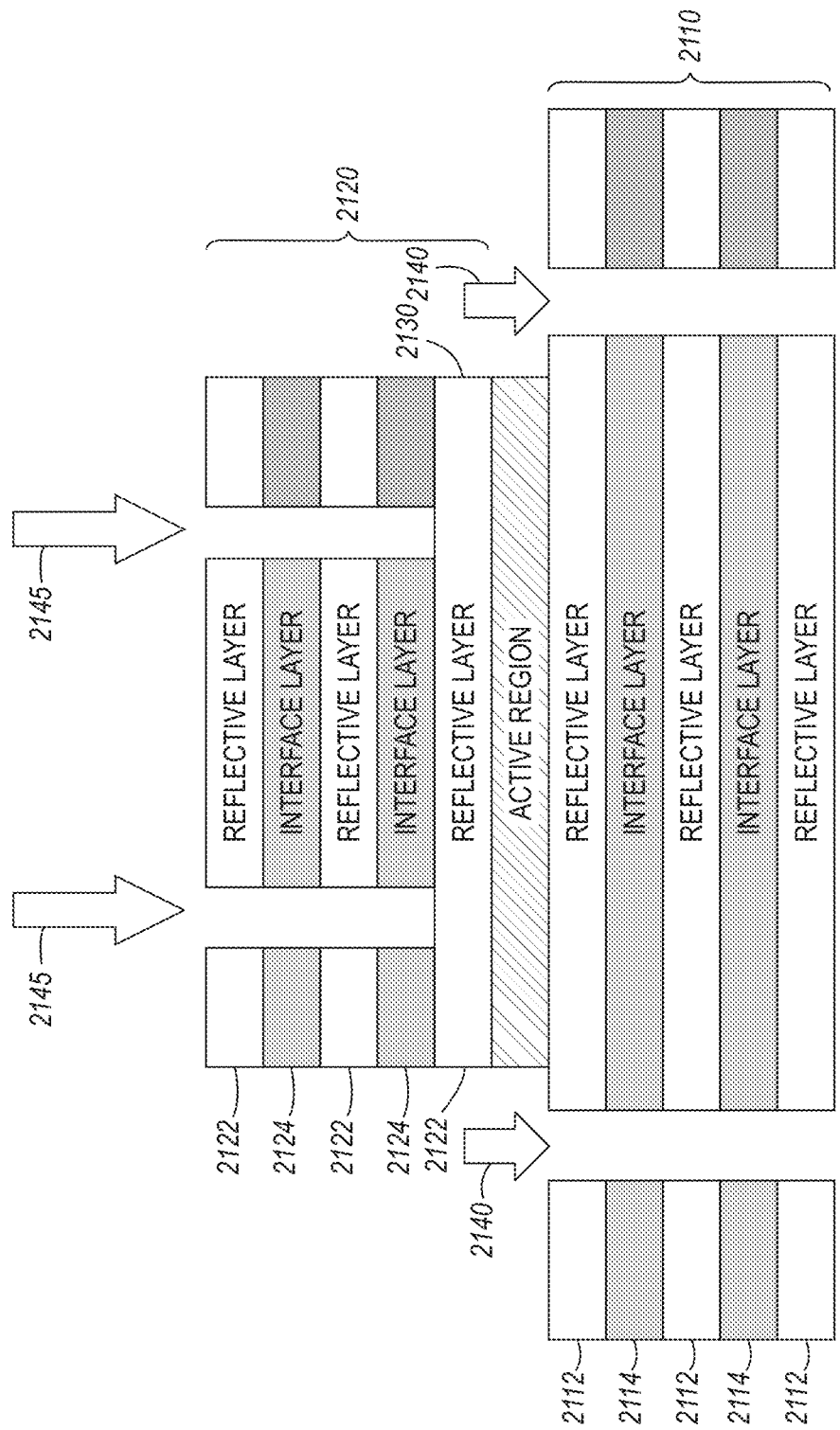
FIG. 21 shows an example of a device in which two sets of vias are used to expose the interstitial layers from the two reflective regions in accordance with embodiments described herein.
Figure 22:
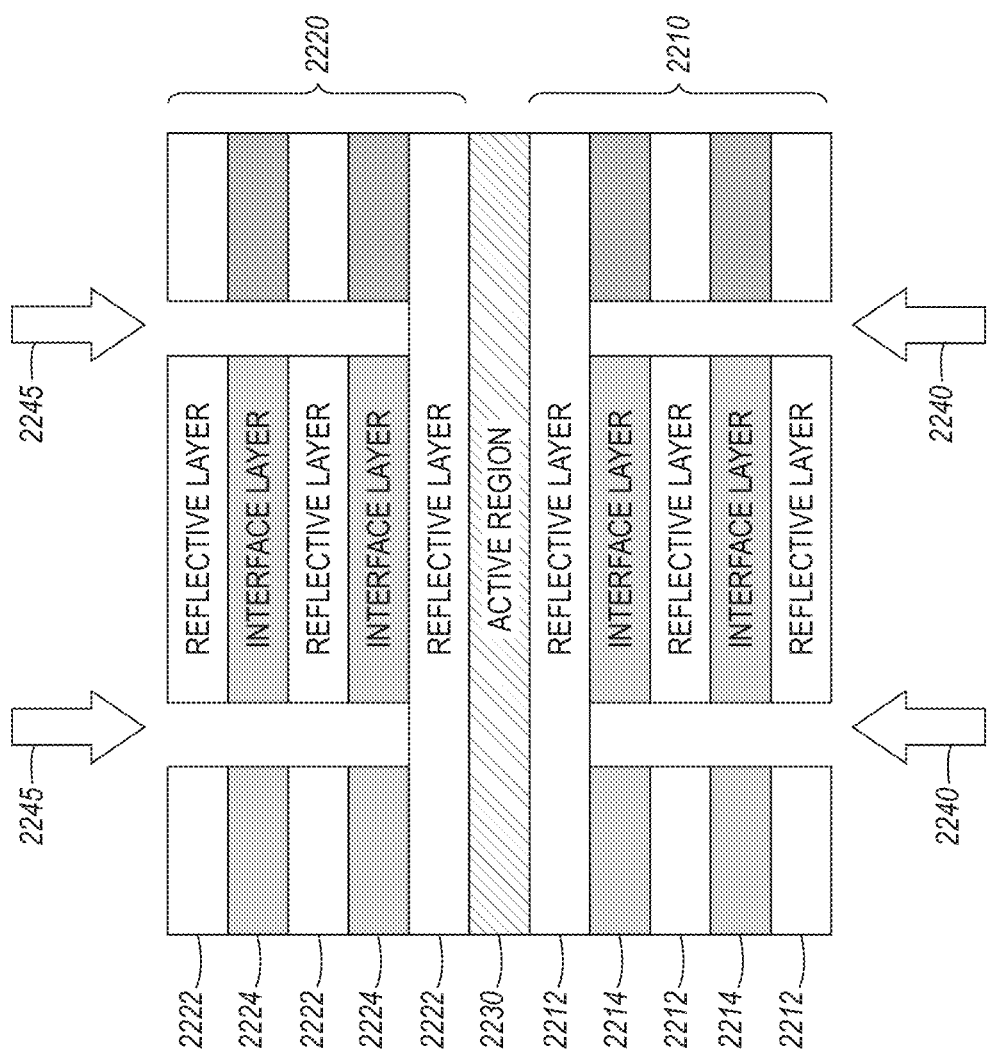
FIG. 22 shows another example of a device in which two sets of vias are used to expose the interstitial layers from the two reflective regions in accordance with various embodiments.

FIGS. 20-22 illustrate examples of via formation to access interstitial layers in a layer stack. FIG. 20 shows a device having a first reflective region 2010, a light emitting layer 2030, and a second reflective region 2020. According to FIG. 20, the first reflective region 2010 comprises one or more reflective layers 2012 alternating with one or more interstitial layers 2014 and the second reflective region 2020 comprises one or more reflective layers 2022 alternating with one or more interstitial layers 2024. A set of vias 2040 are etched to allow access to the interstitial layers by an etchant. In the case of FIG. 20, the vias are created through the top of the device and allow access to the set of interstitial layers 2014 in the first reflective region 2010 and the set of interstitial layers 2024 in the second reflective region 2020. In this example, the vias go through the light emitting layer 2030. Additionally or alternatively, vias may be etched on the bottom side of the device in order to expose the interstitial layers.

FIG. 21 illustrates reflective regions 2110, 2120 and light emitting layer 2130 which are epitaxially grown. A mesa structure is formed allowing vias to be etched to allow access to the interstitial layers of the first reflective region 2140 that do not penetrate the light emitting layer 2130. In some cases, the mesa structure is formed by using a non-selective dry etching process. The mesa structure may also be formed during the growth of the device by masking to prevent epitaxial growth on surfaces at either side of the mesa structure. The second reflective region 2120 may have a different set of vias 2145 that allow access to the interstitial layers 2124 as shown in FIG. 21.

FIG. 22 shows another example of a device that includes first and second reflective regions 2210, 2220 and a light emitting layer 2230. Again, the first and second reflective regions 2210, 2220 each comprise one or more reflective layers 2212, 2222 alternating with one or more interstitial layers 2214, 2224. In this example, the device is grown and two sets of vias 2240, 2245 are formed that allow access to the interstitial layers 2214, 2224 in the first and the second reflective regions 2210, 2220. A first set of vias 2240 are formed below the light emitting layer 2230 penetrating the interstitial layers 2214 of the first reflective region 2210. In some cases, a substrate is removed before creation of the vias 2240. A second set of vias 2245 are formed above the light emitting layer 2230 that expose the interstitial layers 2224 of the first reflective region 2220 to an etchant.

Figure 23:
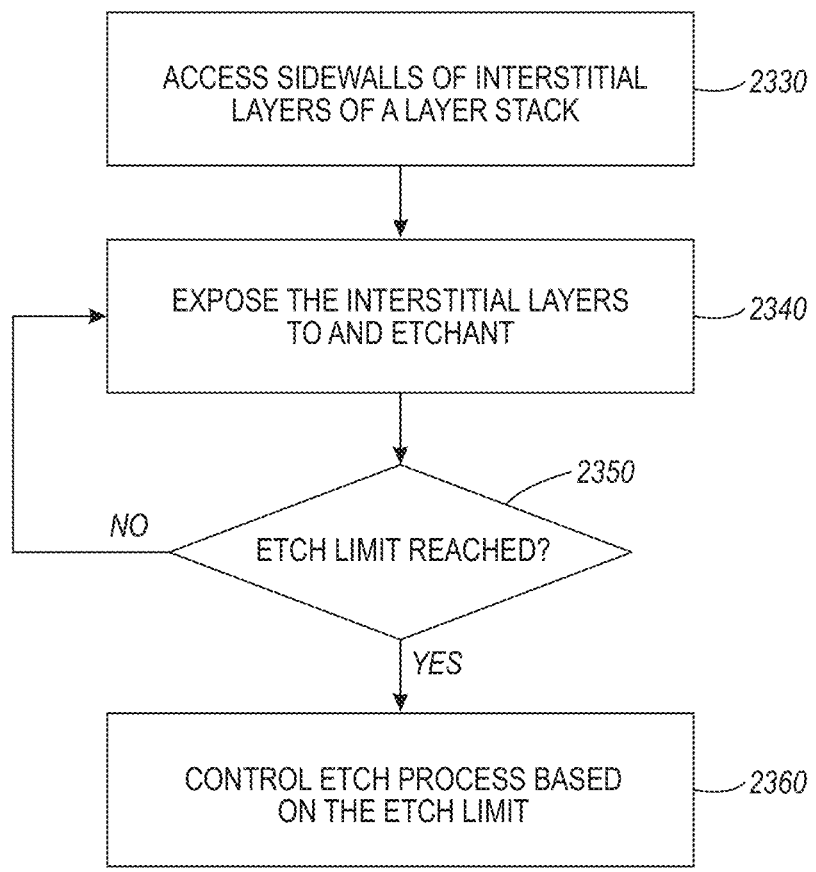
FIG. 23 is a flow diagram of a method for controlling an etch process in accordance with various embodiments.

In some implementations, processes and/or systems used to form reflective regions by etching interstitial layers may involve monitoring and/or controlling the etching process based on a predetermined limit. The system may be fully or partially automatic. In various scenarios, the limit may involve a time period or a detected device characteristic. FIG. 23 is a flow diagram illustrating etch process control. The sidewalls of the interstitial layers of a layer stack are accessed 2330, e.g. by formation of a mesa structure and/or vias. The interstitial layers are exposed 2340 to the etchant. Periodically, the process checks to see of the etch limit has been reached. The etch limit can be a period time, or a device characteristic such as reflectivity of the layer stack or color of the layer stack for example. If the etch limit is reached, the etch process is controlled 2360, e.g., slowed or terminated.

Figure 24:
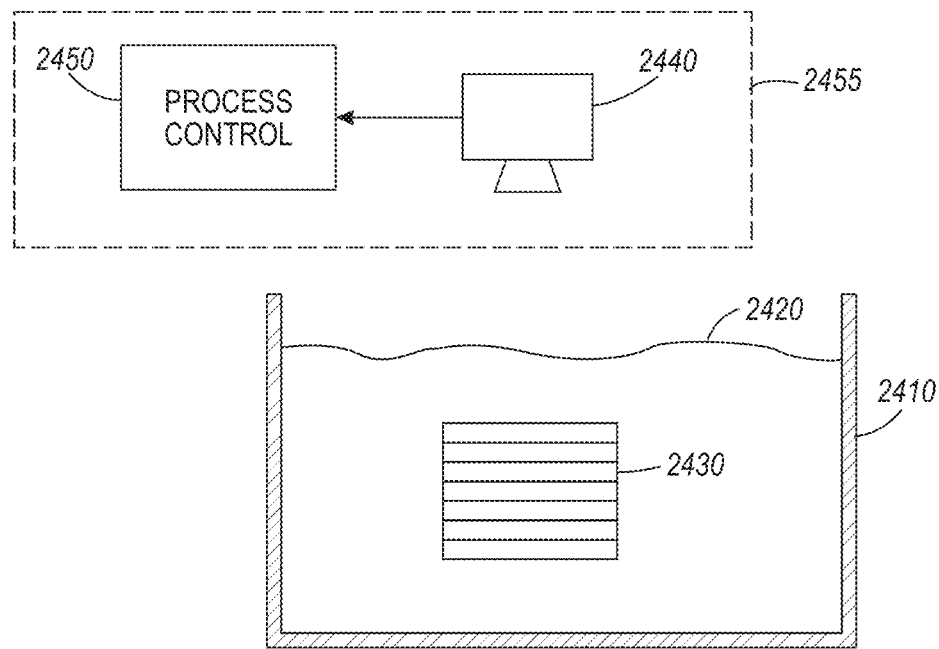
FIG. 24 is a diagram that illustrates a camera-based control system for an etch process in accordance with embodiments discussed herein.
Figure 25:
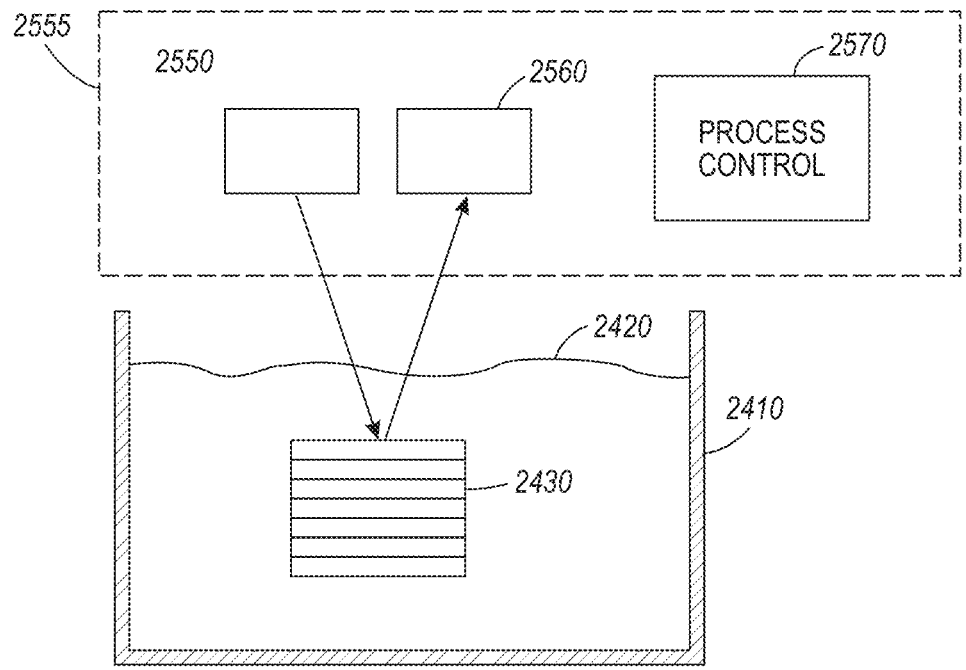
FIG. 25 is a diagram that illustrates a reflectivity-based control system for an etch process in accordance with embodiments described herein.

FIGS. 24 and 25 show systems for etching layer stacks in accordance with various embodiments. Both systems include an etchant tank 2410 configured to contain an etchant 2420. A layer stack 2430 can be submerged in the tank 2410 so that interstitial layers are exposed to the etchant 2420. The system of FIG. 24 includes a control system 2455 that includes a camera 2440. The camera 2440 may include image processor circuitry capable of discerning color changes in the surface of the layer stack 2430 and generating a signal based on color of the layer stack surface. The signal is used by the process control unit 2450 to monitor and/or control the etch process. For example, in some cases, when the signal from the camera 2440 indicates a change in color that exceeds a predetermined etch limit, the process control unit 2450 generates an alert signal and/or terminates the etch process. The control system 2555 of FIG. 25 includes a light source 2550 and detector 2560. Light from the light source 2550 is reflected by the layer stack 2430 during the etch process. The reflectivity of the layer stack 2430 increases as the etching proceeds. Reflected light is detected by a detector 2560 which generates a signal indicative of the reflected light. The process control unit 2570 uses the signal to monitor and/or control the etch process as described above.

In some cases, the DBR structures described herein may be used as sensors and/or may be coupled to other components to form sensing systems. The DBR may be configured so that the optical properties of the DBR, e.g. transmissive and/or reflective properties of the DBR, vary based on the presence and/or characteristics of an analyte occupying in the interstitial gaps between the reflective layers. In some cases, the DBR may be coupled with a laser and properties of the laser, e.g., lasing wavelength, are changed based on the presence and/or characteristics of the analyte.

Figure 26:
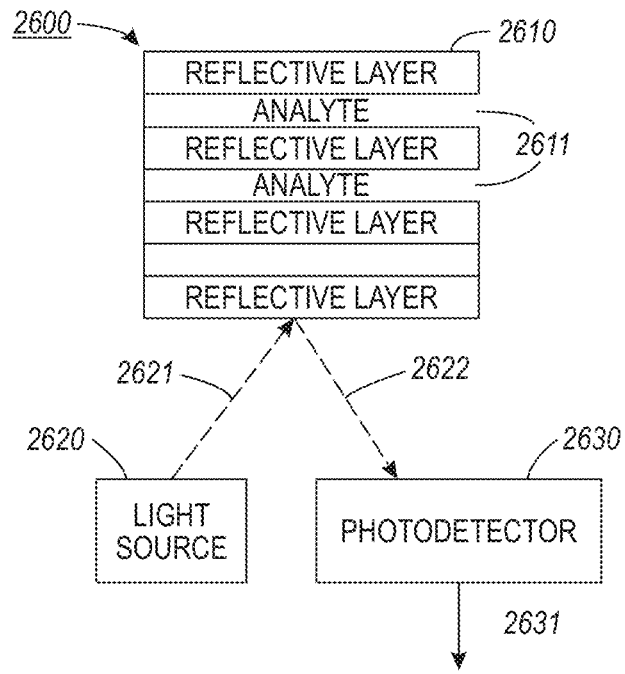
FIG. 26 illustrates a sensor system including a DBR sensor in accordance with various embodiments.

FIG. 26 illustrates a sensing system 2600 that relies on a DBR sensor 2610. The DBR sensor may include one or more material layers in addition to reflective layers. For simplicity, only the reflective layers and the interstitial gaps between the reflective layers of the DBR are shown in FIG. 26. In some cases, the one or more additional material layers may be deposited above and/or below the DBR portion of the sensor. In some cases the DBR and additional layers may form a light emitting device such as a laser.

As illustrated by the system 2600, a DBR sensor 2610 includes of a series of reflective layers and interstitial gaps between the reflective layers. One or more openings 2611 allow entry of an analyte into the interstitial gaps. The system 2600 includes a light source 2620 configured to direct light 2621 toward the DBR sensor 2610. The light source may provide broadband or narrow band light that includes light having the target wavelength of the DBR sensor 2620. Light reflected 2622 by the DBR sensor 2610 is detected by a photodetector 2630 which generates a signal 2631. When an analyte enters through the openings 2611 and into the interstitial gaps between the reflective layers, the refractive index difference between the DBR layers changes. The change in the refractive index difference in turn alters the optical properties of the DBR. For example, the reflectivity of the DBR sensor 2610 may decrease or increase and/or the transmission through the DBR sensor 2610 may increase or decrease. The signal 2631 output from the photodetector 2630 is indicative of the changes in the DBR sensor optical properties. In some implementations, the analyte may be identified based on changes in the signal 2631. For example, if the refractive index of the analyte is known, then the analyte may be identified based on the change in the reflectivity and/or transmissivity of the DBR sensor 2610. In some cases, the sensor system may use a reference cell that is identical in all respects to the DBR sensor except that there are no openings to the interstitial gaps that allow entry of the analyte. The reference cell may be placed in the test environment with the sensor. The system may compare the signal produced by the reference cell to the signal produced by the sensor.

Figure 27:
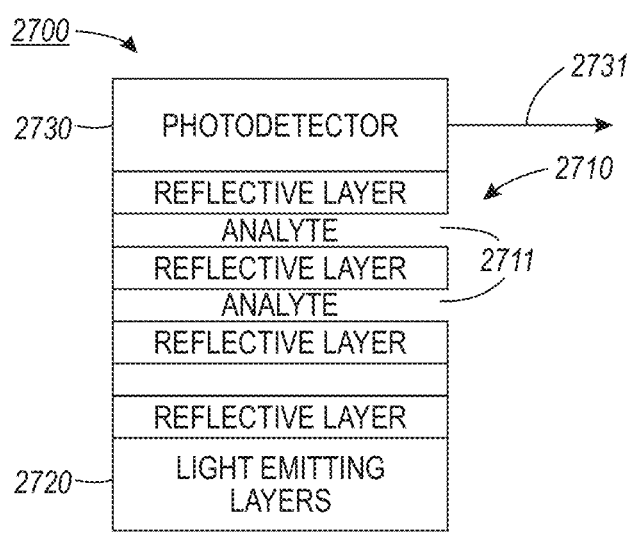
FIG. 27 shows a monolithic layered structure that forms a DBR sensor system in accordance with embodiments described herein.

FIG. 27 illustrates yet another example of a DBR sensor system 2700. In this example, the sensor system 2700 is a monolithic layered structure. A first set of layers forms the DBR sensor portion 2710 including reflective layers and interstitial gaps. Openings 2711 allow analyte to enter at least some of the interstitial gaps. The sensor system 2700 includes light emitting layers 2720 configured to emit light. In some scenarios the light emitted by the light emitting layers 2720 has a wavelength range of about 300 to about 600 nm, although other wavelength ranges may be used in other applications. The sensor system 2700 includes photodetector layers 2730, which, according to the orientation shown in FIG. 27, are disposed on the opposite side of the DBR sensor layers 2710 from the light emitting layers 2720. The photodetector layers 2730 are is configured to sense light emitted by the light emitting layers 2720 and transmitted through the DBR layers 2710.

Assume that the reflective layers of the DBR sensor system 2700-comprise GaN and that initially the interstitial gaps contain air. The reflectivity of the DBR layers 2710 would be relatively high due to the large refractive index difference between the GaN reflective layers and air. When the sensor system 2700 is placed in a test environment, an analyte enters through the openings 2711 and replaces at least some of the air. The analyte has a different (higher) index of refraction than air. Thus, the index of refraction difference between GaN and the analyte contained in the interstitial gaps is lower than the GaN/air refractive index difference. More of the light emitted by the light emitting layers 2720 is transmitted through the DBR layers and reaches the photodetector layers 2730. This alters the output signal 2631 generated by the photodetector layers, indicating the presence of the analyte.

Systems, devices or methods disclosed herein may include one or more of the features, structures, methods, or combinations thereof described herein. For example, a device or method may be implemented to include one or more of the features and/or processes described herein. It is intended that such device or method need not include all of the features and/or processes described herein, but may be implemented to include selected features and/or processes that provide useful structures and/or functionality.

In the foregoing detailed description, numeric values and ranges are provided for various aspects of the implementations described. These values and ranges are to be treated as examples only, and are not intended to limit the scope of the claims. For example, embodiments described in this disclosure can be practiced throughout the disclosed numerical ranges. In addition, a number of materials are identified as suitable for various facets of the implementations. These materials are to be treated as exemplary, and are not intended to limit the scope of the claims. The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

The invention claimed is:

1. A method of making a device, comprising:
   epitaxially growing a layer stack including one or more reflective layers and one or more interstitial layers, each interstitial layer disposed between two reflective layers; and
   forming vias that intersect at least some of the one or more reflective layers and the one or more interstitial layers;
   exposing the interstitial layers to an etchant through the vias;
   etching the interstitial layers;
   detecting a color of the surface of the device, a reflectivity of the device, or both a color of the surface of the device and a reflectivity of the device; and
   controlling the etching based on the detected color, the detected reflectivity, or both the detected color and the detected reflectivity.

2. The method of claim 1, wherein the one or more reflective layers comprises two sets of one or more reflective layers and further comprising growing a light emitting layer between the sets of reflective layers.

3. The method of claim 1, wherein growing the layer stack comprises growing only one reflective layer over or under a light emitting layer.

4. The method of claim 1, wherein:
   forming the vias comprises dry etching the vias; and
   exposing the interstitial layers to the etchant comprises exposing the interstitial layers to a wet etchant through the vias.

5. The method of claim 1, wherein forming the vias comprises forming the vias to surround a central region.

6. The method of claim 1, wherein the reflective layers and the interstitial layers comprise group III-nitride materials.

7. The method of claim 6, wherein the reflective layers and the interstitial layers comprise aluminum (Al) and the reflective layers have a lower Al content than the interstitial layers.

8. The method of claim 1, comprising forming air gaps between the reflective layers.

9. The method of claim 1, wherein etching the interstitial layers further comprises etching the interstitial layers for a predetermined period of time.

* * * * *